United States Patent
Greenspan

(10) Patent No.: US 10,391,074 B2
(45) Date of Patent: Aug. 27, 2019

(54) TOPICAL PREPARATION FOR PAIN RELIEF

(71) Applicant: Sambria Pharmaceuticals, LLC, Atlanta, GA (US)

(72) Inventor: Michael Harvey Greenspan, Dacula, GA (US)

(73) Assignee: Sambria Pharmaceuticals, LLC, Atlanta, GA (US)

( * ) Notice: Subject to any disclaimer, the term of this patent is extended or adjusted under 35 U.S.C. 154(b) by 132 days.

(21) Appl. No.: 14/098,633

(22) Filed: Dec. 6, 2013

(65) Prior Publication Data

US 2014/0163105 A1    Jun. 12, 2014

Related U.S. Application Data

(60) Provisional application No. 61/765,115, filed on Feb. 15, 2013, provisional application No. 61/734,748, filed on Dec. 7, 2012.

(51) Int. Cl.

| | | |
|---|---|---|
| *A61K 31/196* | (2006.01) | |
| *A61K 31/10* | (2006.01) | |
| *A61K 31/08* | (2006.01) | |
| *A61K 45/06* | (2006.01) | |
| *A61K 31/167* | (2006.01) | |
| *A61K 31/245* | (2006.01) | |
| *A61K 31/573* | (2006.01) | |
| *A61K 9/00* | (2006.01) | |

(52) U.S. Cl.
CPC .......... *A61K 31/196* (2013.01); *A61K 9/0014* (2013.01); *A61K 31/08* (2013.01); *A61K 31/10* (2013.01); *A61K 31/167* (2013.01); *A61K 31/245* (2013.01); *A61K 31/573* (2013.01); *A61K 45/06* (2013.01)

(58) Field of Classification Search
CPC ....... A61K 31/196; A61K 31/08; A61K 31/10
USPC ....................................................... 514/567
See application file for complete search history.

(56) References Cited

U.S. PATENT DOCUMENTS

| | | | |
|---|---|---|---|
| 5,270,302 A * | 12/1993 | Shiosaki | C07K 5/0207 514/12.6 |
| 5,650,157 A | 7/1997 | Bockow | |
| 5,709,855 A | 1/1998 | Bockow | |
| 6,201,022 B1 | 3/2001 | Mease et al. | |
| 6,399,039 B2 | 6/2002 | Petrus | |
| 6,416,772 B1 * | 7/2002 | Van Engelen | A61K 9/0014 424/401 |
| 8,420,114 B2 * | 4/2013 | Zanella | A61K 9/0024 424/433 |
| 9,034,298 B2 | 5/2015 | Gruell et al. | |
| 2003/0152637 A1 | 8/2003 | Chasin et al. | |
| 2004/0131665 A1 * | 7/2004 | Wepfer | A61K 9/0014 424/449 |
| 2007/0243132 A1 | 10/2007 | Russell-Jones et al. | |
| 2007/0269379 A1 | 11/2007 | Mitragotri et al. | |
| 2008/0107747 A1 | 5/2008 | Roederer | |
| 2008/0154210 A1 | 6/2008 | Jordan et al. | |
| 2010/0055138 A1 | 3/2010 | Margulies et al. | |
| 2012/0214874 A1 | 8/2012 | Buyuktimkin et al. | |
| 2013/0337031 A1 | 12/2013 | Kisak et al. | |
| 2014/0163105 A1 | 6/2014 | Greenspan | |
| 2015/0290151 A1 | 10/2015 | Birbara et al. | |

FOREIGN PATENT DOCUMENTS

| | | |
|---|---|---|
| WO | 2014130761 A2 | 8/2014 |
| WO | 2014176417 A1 | 10/2014 |

OTHER PUBLICATIONS

International Preliminary Report on Patentability for PCT/US2016/016517; dated Aug. 7, 2018 (6 pages).

* cited by examiner

*Primary Examiner* — Jennifer M Kim
(74) *Attorney, Agent, or Firm* — McCarter & English, LLP; Beverly W. Lubit

(57) ABSTRACT

A composition for pain relief including synergistically effective amounts of an amino benzoate local anesthetic, methylsulfonylmethane (MSM), and ethoxydiglycol. A method of treating pain, by applying the composition to skin in an area of pain, and blocking nerve signals. A method of improving range of motion in an individual, by applying the composition to skin, relieving pain, and allowing the individual to have an improved range of motion at an area of pain.

10 Claims, No Drawings

TOPICAL PREPARATION FOR PAIN RELIEF

BACKGROUND OF THE INVENTION

1. Technical Field

The present invention relates to methods and compositions for pain relief. More specifically, the present invention relates to topical compositions for pain relief.

2. Background Art

Local anesthetics are used in many medical procedures in order to prevent or relieve pain, itching, and burning for a temporary period of time through the blocking of nerve signals and are advantageous when rapid relief is needed. Examples of procedures that local anesthetics are used in include dental procedures such as teeth cleaning and filling cavities, and minor surgeries. Local anesthetics are of two different types, aminoamides and aminoesters. The aminoamides include articaine, bupivacaine, cinchocaine, etidocaine, levobupivacaine, lidocaine, mepivacaine, prilocalne, ropivacaine, and trimecaine. The aminoesters include benzocaine, chloroprocaine, cyclomethycaine, dimethocaine, piperocaine, propoxycaine, procaine, proparacaine, and tetracaine. Local anesthetics can be used topically or injected. Counterirritants (such as menthol, capsaicin, and camphor) are also used to induce local inflammation in order to reduce inflammation in underlying or adjacent tissues.

More specifically, local anesthetics work reversibly binding to and inactivating sodium channels, which produces the effect of inhibiting excitation of nerve endings or by blocking conduction in peripheral nerves. Sodium influx through sodium channels is necessary for depolarization of nerve cell membranes and propagation of impulses along the course of the nerve. Once a nerve loses depolarization and capacity to propagate impulses, sensation in that area is lost. With local anesthetics, it can take several hours to regain sensation in the nerve area. Side effects of local anesthetics can include the feeling that the area of application is swollen, the sensation of feeling cold or hot, rapid heartbeat, and difficulty breathing.

U.S. Pat. Nos. 5,650,157, 5,709,855, and 6,201,022 to Bockow disclose topical analgesic creams that have superior transdermal absorption and absorption speed. Some otherwise desirable oil compositions derived from natural sources are characterized by an unpleasant odor. Fractions or combinations of such oils may also be so characterized. Stable, deodorized oils may be prepared by adding an amount of a deodorizing agent effective to substantially reduce the odor of the derived oil composition, fraction or combination thereof to that oil composition, fraction or combination. The pharmaceutical topical compositions of these patents contain these stable, deodorized oil compositions and exhibit enhanced penetration properties and achieve enhanced patient response. A composition for preventing or treating inflammation and/or pain by topical administration is disclosed. The composition contains an omega fatty acid in combination with spirulina. Preferably, the omega fatty acid is a mixture of omega-3 fatty acids and omega-6 fatty acids. Omega-3 fatty acids include eicosapentaenoic acid and docosahexanoic acid, and omega-6 fatty acids include gamma-linolenic acid and dihomo-gamma-linolenic acid. The composition can further include pharmaceutically acceptable carriers or diluents, vitamins A and E, and a cyclooxygenase inhibitor such as methyl salicylate. The pharmaceutical compositions can be used to manage pain and/or to treat the underlying ailments. Methods of making such topical pharmaceutical compositions are also discussed.

There remains a need for a safe and effective topical local anesthetic for the relief of pain and also to improve range of motion in individuals suffering from pain.

SUMMARY OF THE INVENTION

The present invention provides for a composition for pain relief including synergistically effective amounts of an amino benzoate local anesthetic, methylsulfonylmethane (MSM), and ethoxydiglycol.

The present invention provides for a method of treating pain, by applying the composition to skin in an area of pain, and blocking nerve signals.

The present invention also provides for a method of improving range of motion in an individual, by applying the composition to skin, relieving pain, and allowing the individual to have an improved range of motion at an area of pain.

DETAILED DESCRIPTION OF THE INVENTION

The present invention provides generally for a topical composition for treating pain and improving range of motion.

As used herein, "pain relief" refers to the ability to reduce and/or eliminate the feeling of pain in the body in order to reduce suffering and improve the quality of life of an individual. The composition of the present invention provides pain relief for a variety of conditions, further described below.

As used herein, "blocking nerve signals" refers to the interruption of pain signals sent to an individual's brain. The composition of the present invention blocks nerve signals such that the nerves lose depolarization and capacity to propagate impulses and therefore sensation in the area of application of the composition is lost and pain relief is provided. The nerves are essentially numbed in the area of application.

The composition preferably includes an amino benzoate local anesthetic, methylsulfonylmethane (MSM), and ethoxydiglycol. These three components work together synergistically to relieve pain where the composition is applied. In other words, the effect of the three components together is more than additive. Therefore, lower amounts of each of these components can be used than would normally be used alone to achieve the results of pain relief. Furthermore, the three components unexpectedly result in deep penetration of the active ingredients (i.e. the amino benzoate), resulting in effective analgesia. The composition is able to quickly and effectively travel through an individual's skin due to the three components of the composition acting in synergy. The amino benzoate local anesthetic blocks nerve signals where applied.

Many different amino benzoate local anesthetics can be used, such as, but not limited to, lidocaine, benzocaine 5-10%, prilocalne 1%, tetracaine 2%, and combinations thereof.

The amino benzoate local anesthetic is preferably lidocaine (or lidocaine HCl), also known as 2-(diethylamino)-N-(2,6-dimethylphenyl)acetamide shown in Formula (I).

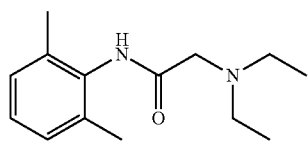

Lidocaine can be administered in amounts of 0.5 to 4.5 mg/kg/dose. Other amino benzoate local anesthetics with similar dosing include tetracaine (2-(dimethylamino)ethyl 4-(butylamino)benzoate), shown in Formula (II), and benzocaine (ethyl 4-aminobenzoate), shown in Formula (III).

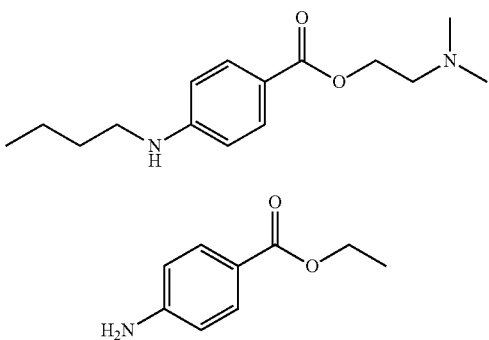

MSM (formula $(CH_3)_2SO_2$) is an organosulfur compound, and also known as $DMSO_2$, methyl sulfone, and dimethyl sulfone. MSM is currently available as a dietary supplement for osteoarthritis. MSM can be administered in up to 6 g/day.

Ethoxydiglycol is a cosmetic grade solvent and carrier that is used to provide an even distribution of the ingredients throughout a product.

The composition can further include various carriers and excipients such as, but not limited to, water, polyacrylamide (a flocculant), C13-14 isoparaffin (an emollient), laureth-7 (surfactant and emulsifier), propylene glycol (penetration enhancer), triethanolamine (pH balancer), emu oil (antifungal agent), tea tree oil (antifungal agent), *arnica Montana* extract (anti-inflammatory), ethylhexylglycerin (deodorizing agent), phenoxyethanol (bactericide), isopropyl palmitate (emollient, moisturizer, thickening agent, anti-static), stearic acid (surfactant and softening agent), glucosamine sulfate (anti-arthritic), chondroitin sulfate (anti-arthritic), and combinations thereof. An example formulation is provided in Table 1, along with possible ranges for the components. Any other suitable excipients in these categories can also be used.

TABLE 1

| Ingredient | Amount | Range |
|---|---|---|
| Deionized water | QS | 1-50% |
| Polyacrylamide, C13-14 isoparaffin, laureth-7 | 6.50% | 1-20% |
| Lidocaine HCl | 4.00% | 1-20% |
| Methylsulfonylmethane (MSM) | 3.00% | 1-10% |
| Ethoxydiglycol | 1.00% | 0.10-5% |
| Propylene Glycol | 1.00% | 0.10-5% |
| Triethanolamine | 0.90% | 0.10-5% |
| Emu Oil | 0.25% | 0.10-5% |
| Tea Tree Oil | 0.20% | 0.10-5% |

TABLE 1-continued

| Ingredient | Amount | Range |
|---|---|---|
| *Arnica Montana* Extract | 0.50% | 0.10-5% |
| Ethylhexylglycerin | 0.40% | 0.10-5% |
| Phenoxyethanol | 0.40% | 0.10-5% |
| Isopropyl Palmitate | 0.20% | 0.10-5% |
| Stearic Acid | 0.15% | 0.05-5% |
| Glucosamine Sulfate | 0.10% | 0.05-5% |
| Chondroitin Sulfate | 0.10% | 0.05-5% |

The topical composition can be in any number of forms. Preferably, the topical composition is a cream or gel that can be applied to an affected area of the skin. The topical composition can be in the form of a patch that releases the composition into the skin. The topical composition can also be a spray (aerosol or non-aerosol). The topical composition can be in an oral form with suitable diluents, solvents, and/or carriers. Different release profiles can be achieved with different forms, such as rapid release, extended release, or sustained release. The topical composition can be applied multiple times a day, once per day, or as often as needed.

The composition can be used to treat pain. Examples of conditions that can require pain relief include, but are not limited to, tears, tendonosis, and supraspinatus acute and/or chronic tendonitis. The composition is particularly suited to relieve pain associated with rotator cuff disease in individuals for whom surgical intervention is not currently indicated. In tendonitis, the composition can be used in acute conditions in order to reduce or halt the compliment cascade (kinins) and help reduce nociception. In tendonosis, there are more likely to be fibrous adhesions involved, and the composition can help relieve pain while a medical practitioner breaks up the adhesions. The composition is also particularly suited for neck and low back pain. The composition can also be used to treat pain caused by herpes zoster (shingles), insect bites, stings, neuropathy, and migraine headaches. The composition can also be used to provide an individual with an increased range of motion or function due to pain relief.

The present invention provides generally for a method of treating pain, by applying the composition to skin in an area of pain, and blocking nerve signals. A synergistically effective amount of the composition is used. The composition deeply penetrates into the skin to provide effective pain relief.

The present invention also provides for a method of improving range of motion in an individual, by applying the composition to skin, relieving pain, and allowing the individual to have an improved range of motion at an area of pain. A synergistically effective amount of the composition is used. By relieving pain in the individual through blocking nerve signals, they can regain motion at the site of pain.

The present invention provides for a method of treating post-herpetic neuralgic pain, by applying the composition to skin in an area of pain. Preferably, in this method, the composition includes lidocaine 4% (or in a range of 5% to 10%, especially if the patient has a prescription), and/or benzocaine in a range of 15% to 20%.

The present invention provides for a method of treating peripheral neuropathy caused by diabetes I, by applying the composition to skin in an area of pain. Preferably, in this method, the composition includes lidocaine 4% (or in a range of 5% to 10%, especially if the patient has a prescription), and/or benzocaine in a range of 15% to 20%.

The present invention provides for a method of treating insect bites and stings and related pain, by applying the composition to skin in an area of pain. Preferably, in this method, the composition includes lidocaine 4% (or in a range of 5% to 10%, especially if the patient has a prescription), and/or benzocaine in a range of 15% to 20%. The composition can further include cortisone or hydrocortisone in the range of 0.5% to 1% to provide an anti-inflammatory effect.

The present invention provides for a method of treating migraine headaches, by applying the composition to skin in an area of pain. Preferably, in this method, the composition includes lidocaine 4% (or in a range of up to 5%, especially if the patient has a prescription). The composition can further include a vasoconstrictor and/or anti-inflammatory agent to provide an anti-inflammatory effect. Migraines can be caused by abnormal blood circulation from tightened muscles around blood vessels. The composition acts to relax muscles that otherwise constrict around vessels blocking circulation and around nerves being impinged. This action provides relief from migraine pain. The composition can be applied at various sites on an individual depending on the location of the migraine.

In any of the above methods, the composition can be co-administered with any other suitable anti-pain and anti-inflammatory agent to work in combination with and synergistically with the co-administered therapeutics in the composition. For example, in treating migraine, the composition can be administered in combination with the administration of non-steroidal anti-inflammatory drugs (NSAIDS) such as, but not limited to, acetaminophen, salicylates (aspirin, diflunisal, salsalate), acetic acid derivatives (indomethacin, ketorolac, sulindac etodolac, diclofenac, nabumetone), propionic acid derivatives (ibuprofen, naproxen, flurbiprofen, ketoprofen, oxaprozin, fenoprofen, loxoprofen), fenamic acid derivatives (meclofenamic acid, mefenamic acid, flufenamic acid, tolfenamic acid), oxicam (enolic acid) derivatives (piroxicam, meloxicam, tenoxicam, droxicam, lornoxicam, isoxicam), arylalkanoic acid derivatives (tolmetin); or selective COX-2 inhibitors (celecoxib, rofecoxib, valdecoxib, parecoxib, lumiracoxib, etoricoxib, firocoxib), steroids, or lidocaine administrations such as injections, etc. Counterirritants (such as menthol, capsaicin, and camphor) can be administered. Also, the treatment can be multi-site, by administering the present invention at the temples, injections in the back of the neck, or other suitable sites on the body such as in an effort to relieve a migraine by a multi-focal regimen.

The compound of the present invention is administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

In the method of the present invention, the compound of the present invention can be administered in various ways. It should be noted that it can be administered as the compound and can be administered alone or as an active ingredient in combination with pharmaceutically acceptable carriers, diluents, adjuvants and vehicles. The patient being treated is a warm-blooded animal and, in particular, mammals including man. The pharmaceutically acceptable carriers, diluents, adjuvants and vehicles as well as implant carriers generally refer to inert, non-toxic solid or liquid fillers, diluents or encapsulating material not reacting with the active ingredients of the invention.

The doses can be single doses or multiple doses over a period of several days. The treatment generally has a length proportional to the length of the disease process and drug effectiveness and the patient species being treated.

Throughout this application, various publications, including U.S. patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

What is claimed is:

1. A method of reducing a sensation of pain in a subject, comprising:
    applying topically directly to skin of the subject over an area of pain a therapeutic amount of a composition comprising
    (a) lidocaine in an amount of about 1% to about 20%; and
    (b) a penetration enhancer comprising a penetration-enhancing amount of a methylsulfonylmethane (MSM) component, and an ethoxydiglycol component, wherein the amount of the MSM component is about 1% to about 10%, and the amount of the ethoxydiglycol component is about 0.10% to about 5%,
    wherein the composition is effective
    (i) to deeply penetrate the skin of the subject,
    (ii) to remain in the skin and block nerve signals affecting sensation of pain, and
    (iii) to provide pain relief.

2. The method of claim 1, wherein the pain is caused by a condition selected from the group consisting of a tear, tendonosis, supraspinatus acute tendonitis, chronic tendonitis, rotator cuff disease, neck and low back pain, herpes zoster, insect bites and stings, neuropathy, and migraine headaches.

3. The method of claim 1, wherein the pain is caused by insect bites and stings, the composition further includes a therapeutic selected from the group consisting of cortisone and hydrocortisone, and the therapeutic amount is effective to provide an anti-inflammatory effect.

4. The method of claim 1, wherein the pain is caused by migraine headaches, the composition further includes a therapeutic selected from the group consisting of a vasoconstrictor, an anti-inflammatory agent, and combinations thereof, and the therapeutic amount is effective to provide an anti-inflammatory effect.

5. The method of claim 1, wherein the pain is caused by migraine headaches and the therapeutic effect further includes relaxing muscles that otherwise constrict around vessels blocking circulation and around nerves being impinged.

6. The method of claim 1, wherein the administering is at multiple sites of the body.

7. The method of claim 1, further including administering an anti-pain and anti-inflammatory agent selected from the group consisting of acetaminophen, aspirin, diflunisal, salsalate, indomethacin, ketorolac, sulindac, etodolac, diclofenac, nabumetone, ibuprofen, naproxen, flurbiprofen, ketoprofen, oxaprozin, fenoprofen, loxoprofen, meclofenamic acid, mefenamic acid, flufenamic acid, tolfenamic acid, piroxicam, meloxicam, tenoxicam, droxicam, lornoxicam, isoxicam, tolmetin, celecoxib, rofecoxib, valdecoxib, parecoxib, lumiracoxib, etoricoxib, firocoxib, steroids, and lidocaine.

8. A method of improving range of motion in an individual, including applying topically directly to the skin of the individual over an area of pain a therapeutic amount of a composition comprising
   (a) lidocaine in an amount of about 1% to about 20%, and
   (b) a penetration enhancer comprising a penetration-enhancing amount of a methylsulfonylmethane (MSM) component and a ethoxydiglycol component, wherein the amount of the MSM component is about 1% to about 10%, and the amount of the ethoxydiglycol component is about 0.10% to about 5%;

wherein the composition is effective
   (i) to deeply penetrate the skin of the subject,
   (ii) to remain in the skin of the subject and block nerve signals affecting sensation of pain; and
   (iii) to improve range of motion at the area of pain by providing pain relief in the area of pain.

9. The method of claim 8, further including administering an anti-pain and anti-inflammatory agent selected from the group consisting of acetaminophen, aspirin, diflunisal, salsalate, indomethacin, ketorolac, sulindac, etodolac, diclofenac, nabumetone, ibuprofen, naproxen, flurbiprofen, ketoprofen, oxaprozin, fenoprofen, loxoprofen, meclofenamic acid, mefenamic acid, flufenamicacid, tolfenamic acid, piroxicam, meloxicam, tenoxicam, droxicam, lornoxicam, isoxicam, tolmetin, celecoxib, rofecoxib, valdecoxib, parecoxib, lumiracoxib, etoricoxib, firocoxib, steroids, and lidocaine.

10. The method of claim 1, wherein the lidocaine is present in an amount of about 4% to about 10%.

* * * * *